United States Patent
Olabisi et al.

(10) Patent No.: US 11,278,597 B2
(45) Date of Patent: Mar. 22, 2022

(54) COMPOSITIONS AND METHODS FOR WOUND HEALING

(71) Applicant: RUTGERS, THE STATE UNIVERSITY OF NEW JERSEY, New Brunswick, NJ (US)

(72) Inventors: Ronke Olabisi, Santa Monica, CA (US); Ayesha Aijaz, Piscataway, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 193 days.

(21) Appl. No.: 16/493,896

(22) PCT Filed: Mar. 16, 2018

(86) PCT No.: PCT/US2018/022859
§ 371 (c)(1),
(2) Date: Sep. 13, 2019

(87) PCT Pub. No.: WO2018/170394
PCT Pub. Date: Sep. 20, 2018

(65) Prior Publication Data
US 2020/0085914 A1    Mar. 19, 2020

Related U.S. Application Data

(60) Provisional application No. 62/472,725, filed on Mar. 17, 2017.

(51) Int. Cl.
*A61K 38/28* (2006.01)
*A61K 35/28* (2015.01)
*A61K 9/00* (2006.01)
*A61K 9/70* (2006.01)
*A61K 9/06* (2006.01)
*A61P 17/02* (2006.01)

(52) U.S. Cl.
CPC ............ *A61K 38/28* (2013.01); *A61K 9/0014* (2013.01); *A61K 9/06* (2013.01); *A61K 9/70* (2013.01); *A61K 35/28* (2013.01); *A61P 17/02* (2018.01)

(58) Field of Classification Search
None
See application file for complete search history.

(56) References Cited

U.S. PATENT DOCUMENTS

| 10,335,514 B2 * | 7/2019 | Iwazawa ............. A61L 27/3886 |
| 2003/0017969 A1 | 1/2003 | Tennenbaum et al. ........... 514/3 |

(Continued)

FOREIGN PATENT DOCUMENTS

WO    WO-2016052504 A1 *    4/2016    ............... A61K 9/16

OTHER PUBLICATIONS

O'Loughlin, Aonghus; et al; "Topical Administration of Allogeneic Mesenchymal Stem Cells Seeded in a Collagen Scaffold Augments Wound Healing and Increases Angiogenesis in the Diabetic Rabbit Ulcer" Diabetes, 61, A604, 2013 (Year: 2013).*

(Continued)

*Primary Examiner* — David W Berke-Schlessel
(74) *Attorney, Agent, or Firm* — Licata & Tyrrell P.C.

(57) ABSTRACT

Compositions of insulin-secreting cells and stem cells and methods for their use as well as use of insulin and stem cell products in wound healing and/or reducing scar and/or scab formation are provided.

17 Claims, 10 Drawing Sheets

(56) References Cited

U.S. PATENT DOCUMENTS

| | | | |
|---|---|---|---|
| 2005/0019865 A1 | 1/2005 | Kihm et al. | 435/69.1 |
| 2006/0177418 A1 | 8/2006 | Braiman-Wiksman et al. | 424/85.1 |

OTHER PUBLICATIONS

Yeung, Telford Y; et al.; "Human Mesenchymal Stem Cells Protect Human Islets from Pro-Inflammatory Cytokines" PLoS One, 7, e38189, 2012 (Year: 2012).*

Aijaz, Ayesha; et al.; "Coencapsulation of ISCs and MSCs Enhances Viability and Function of both Cell Types for Improved Wound Healing" Cellular and Molecular Bioengineering, 12, 481-493, 2019 (Year: 2019).*

Aijaz et al. "Hydrogel Microencapsulated Insulin-Secreting Cells Increase Keratinocyte Migration, Epidermal Thickness, Collagen Fiber Density, and Wound Closure in a Diabetic Mouse Model of Wound Healing" Tissue Eng Part A. 2015 21(21-22) :2723-32.

Faulknor et al. "Mesenchymal stromal cells reverse hypoxia-mediated suppression of a-smooth muscle actin expression in human dermal fibroblasts" Biochem Biophys Res Commun 2012 458(1):8-13.

Figliuzzi et al. "Mesenchymal stem cells help pancreatic islet transplantation to control type 1 diabetes" World J Stem Cells. 2014 6(2):163-72.

Hrynyk et al. "Alginate—PEG sponge architecture and role in the design of insulin release dressings" Biomacromolecules 2012 13:1478-1485.

Kim et al. "Therapeutic potential of mesenchymal stem cells for oral and systemic diseases" Dent Clin. North Am. 2012 56(3):651-675.

Lee et al. "Mesenchymal stem cells and cutaneous wound healing: novel methods to increase cell delivery and therapeutic efficacy" Stem Cell Research & Therapy 2016 7:37 pp. 1-8.

Lima et al. "Topical insulin accelerates wound healing in diabetes by enhancing the AKT and ERK pathways: a double-blind placebo-controlled clinical trial" PLoS One 2012 7(5): e36974.

Liu et al. "Cell and molecular mechanisms of keratinocyte function stimulated by insulin during wound healing" BMC Cell Biol. 2009 10 pp. 1-15.

Patel et al. "Therapeutic potential of mesenchymal stem cells in regenerative medicine" Stem Cells International 2013 Article ID 496218 pp. 1-15.

Pileggi, A. Mesenchymal stem cells for the treatment of diabetes Diabetes 2012 61(6):1355-1356.

Sordo, V & Piemonti, L. "Mesenchymal stem cells as feeder cells for pancreatic islet transplants" Rev Diabet Stud. 2010 Summer;7(2):132-43.

Turner N. "Mitochondrial Metabolism and Insulin Action" 2013 Chapter 4 pp. 71-114.

Vojtassák et al. "Autologous biograft and mesenchymal stem cells in treatment of the diabetic foot" Neuro Endocrinol Lett 2006 27 Suppl 2:134-7.

Yoshikawa et al. "Wound iherapy by marrow mesenchymal cell transplantation" Plast Reconstr Surg 2008 121(3):860-77.

International Search Report and Written Opinion in PCT/US18/22859 dated Jun. 1, 2018.

International Preliminary Report on Patentability in PCT/US18/22859 dated Sep. 17, 2019.

* cited by examiner

COMPOSITIONS AND METHODS FOR WOUND HEALING

This patent application is the National Stage of International Application No. PCT/US2018/022859 filed Mar. 16, 2018, which claims the benefit of priority from U.S. Provisional Application Ser. No. 62/472,725 filed Mar. 17, 2017, the contents of each of which are herein incorporated by reference in their entirety.

FIELD

The present invention relates to compositions of insulin-secreting cells and stem cells and methods for their use in combination in wound healing.

BACKGROUND

Chronic wounds affect more than 6 million people in the United States alone. Diabetic foot ulcers, in particular, constitute a devastating subset of chronic wounds and are a significant source of morbidity and mortality in diabetic patients.

Chronic wounds are characterized by prolonged inflammation-defective immune cell function, decreased re-epithelialization, reduced collagen synthesis and impaired neovascularization.

Application of topical insulin creams and crystalline insulin-loaded PLGA alginate-PEG sponge dressings have been shown to regulate inflammation, promote angiogenesis and increase collagen synthesis and re-epithelialization in chronic wounds (Y. Liu, BMC Cell Biol. 2009 10; Lima MHM, PLoS ONE 2012 7(5): e36974; and Turner N. Mitochondrial Metabolism and Insulin Action 2013 doi: 10.5772/56449). However, application of topical ointments requires repeated application and has a potential for reinjury as well as a propensity to infection while hydrolysis products of degradable polymers in the sponge dressing reduced insulin bioactivity over time (Lima MHM PLoS ONE 2012 7(5):e36974; Hrynyk M, Biomacromolecules 2012 13:1478-1485).

Hydrogel microencapsulated insulin-secreting cells (ISCs) have been disclosed to assist in the advancement of wound healing in a mouse model (Aijaz et al. Tissue Eng Part A. 2015 November; 21(21-22):2723-32. Epub 2015 Sep. 11).

Mesenchymal stem cells (MSCs) have also been disclosed to have benefits in wound healing (see, for example, Patel et al. Stem Cells International, vol. 2013, Article ID 496218, 15 pages, 2013. doi:10.1155/2013/496218) and in particular in diabetic wounds. Mesenchymal stem cells accelerate wound healing through ECM synthesis and wound contraction remodeling, promotion of angiogenesis, regulation of inflammation and proliferation of endothelial cells, fibroblasts and keratinocytes (Vojtassák J. Neuro Endocrinol Lett 2006 27 Suppl 2:134-7; Yoshikawa T. Plast Reconstr Surg 2008 121(3):860-77; Faulknor R A. Biochem Biophys Res Commun 2012 458(1):8-13).

Further, MSCs have been disclosed to differentiate into ISCs to accelerate wound healing (Pileggi, A. Diabetes 2012 61(6):1355-1356 and Kim et al. Dent Clin. North Am. 2012 56(3):651-675).

Two primary roadblocks to widespread MSC use in wound healing has been their tendency to migrate from target wounds in search of other sites in need of repair and even when prevented from migration by encapsulation strategies, most transplanted MSCs apoptose shortly following transplantation (Chen et al. Tissue Engineering Part B: Reviews 2013 19(6): 516-528).

In addition, MSCs have been proposed for use as as feeder cells for intraperitoneal pancreatic islet transplants. In these studies, MSCs were co-transplanted with ISCs for the maintenance of normal glucose levels and treatment of diabetes (Rev Diabet Stud. 2010 Summer;7(2):132-43. doi: 10.1900/RDS.2010.7.132.) MSCs have also been disclosed to have potential to enhance islet transplantation to control type a diabetes by suppressing inflammatory damage and immune mediated rejection (World J Stem Cells. 2014 Apr. 26;6(2): 163-72. doi: 10.4252/wjsc.v6.i2.163). Coencapsulation of these cells to control blood sugar levels has been performed for over a decade.

SUMMARY

An aspect of the present invention relates to a composition comprising insulin-secreting cells and stem cells. In one nonlimiting embodiment, the composition is formulated for topical application. In one nonlimiting embodiment, the insulin-secreting cells and the stem cells of the composition are coencapsulated. In one nonlimiting embodiment, the insulin-secreting cells and the stem cells are in a hydrogel dressing. In one nonlimiting embodiment, the insulin-secreting cells and the stem cells of the composition are coencapsulated in a hydrogel. In one nonlimiting embodiment, the insulin-secreting cells and the stem cells are microencapsulated.

Another aspect of the present invention relates to a method for healing a wound in a subject by applying a composition comprising insulin-secreting cells and stem cells to a wound site of the subject. In one nonlimiting embodiment, the composition is formulated for topical application. In one nonlimiting embodiment, the insulin-secreting cells and the stem cells are coencapsulated in the composition applied to the wound site. In one nonlimiting embodiment, the insulin-secreting cells and the stem cells are in a hydrogel dressing applied to the wound site. In one nonlimiting embodiment, the insulin-secreting cells and the stem cells are coencapsulated in a hydrogel dressing applied to the wound site. In one nonlimiting embodiment, the insulin-secreting cells and the stem cells are microencapsulated.

Another aspect of the present invention relates to a method for producing re-epithelialization at the wound site by applying to the wound site a composition comprising insulin-secreting cells and stem cells.

Another aspect of the present invention relates to a method for accelerating wound healing at a wound site by applying to the wound site a composition comprising insulin-secreting cells and stem cells.

Another aspect of the present invention relates to a method for reducing scar formation at a wound site in a subject by applying to the wound site a composition comprising insulin-secreting cells and stem cells.

Yet another aspect of the present invention relates to a method for reducing scab formation at a wound site in a subject by applying to the wound site a composition comprising insulin-secreting cells and stem cells.

DETAILED DESCRIPTION

Figure 1:
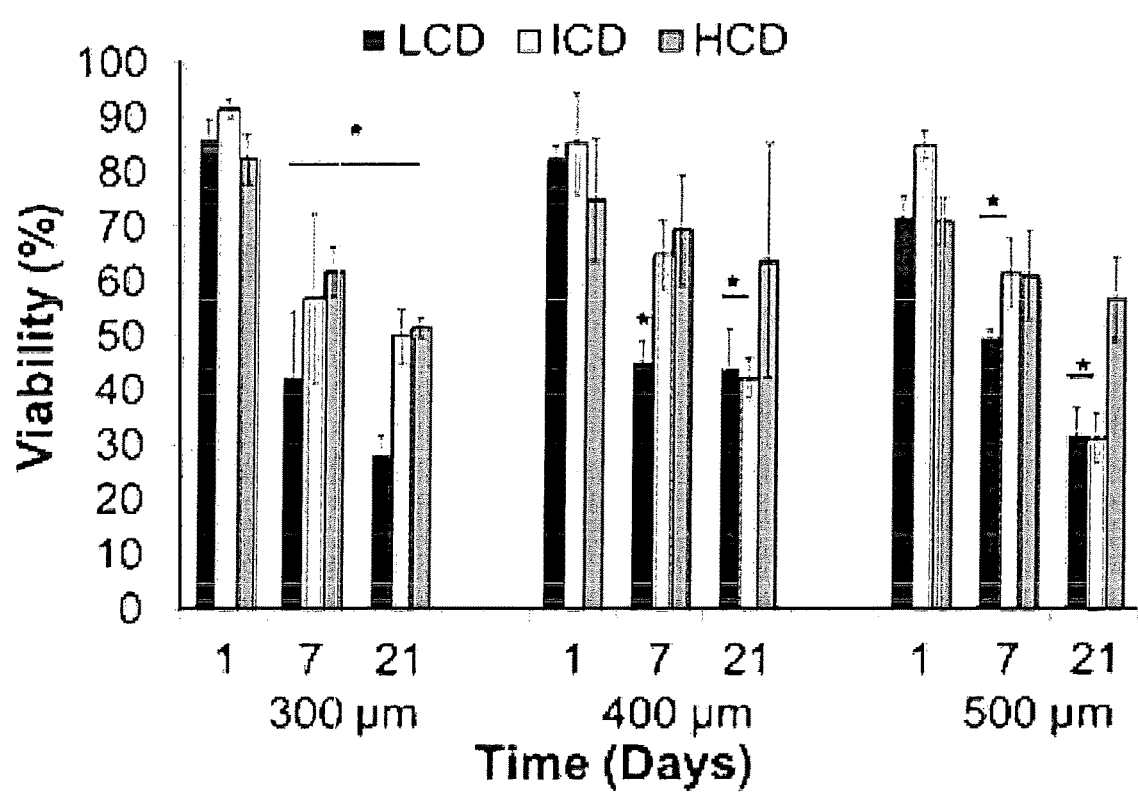
FIG. 1 is a bargraph depicting results of assessment of ISC cell viability at low, intermediate and high cell density on hydrogel sheets of 300, 400 and 500 µm thickness.

This disclosure relates to compositions and methods for use of these compositions in healing of wounds.

The compositions of the present invention comprise insulin-secreting cells (ISCs) and stem cells.

Various sources for the cells exist.

In one nonlimiting embodiment, ISCs may be genetically modified cells that produce insulin in a constant rate with donor insulin. In another embodiment, the ISCs may comprise islet cells harvested from the pancreas. However, the present invention is in no way limited to a particular tissue source for the cells.

By stem cells, as used herein, it is meant to include any undifferentiated cell of a multicellular organism that is capable of giving rise to indefinitely more cells of the same type, and from which certain other kinds of cell arise by differentiation. Nonlimiting examples of stem cells useful in the present invention include, but are not limited to, mesenchymal stem cells (MSCs), embryonic stem cells (ESCs), induced pluripotent stem cells (iPSCs), hematopoietic stem cells, adipose-derived stem cells, endothelial stem cells, dental-pulp derived, bone marrow stromal cells, muse cells and amniotic stem cells. In one nonlimiting embodiment, the stem cells are MSCs.

Various ranges of cell densities and ratios of the combination of cells can be used. In one nonlimiting embodiment, the combination of cells is included in the composition in an amount effective to produce re-epithelialization at the wound site.

In one nonlimiting, the cell density ranges from about $0.5 \times 10^6$ cells to about $5 \times 10^6$ cells per $cm^2$. However, as will be understood by the skilled artisan upon reading this disclosure, such ranges may be modified depending upon the dressing size.

In one nonlimiting embodiment, the cell density is about $0.5 \times 10^6$ cells per $cm^2$.

In one nonlimiting embodiment, the ratio of ISCs to stem cells ranges from 1:10 to 10:1.

In one nonlimiting embodiment, the ratio of ISCs to stem cells is 1:1. As demonstrated herein, a 1:1 ratio of ISCs:MSCs exhibits superior insulin and MSC factor secretion as compared to other ISC:MSC coencapsulation constructs. Further, addition of the MSCs is demonstrated herein to improve the insulin secretory function of ISCs, and vice versa.

In one nonlimiting embodiment, the ISCs and stem cells are formulated together for topical application. Any formulation which accomplishes direct contact between the composition of the present invention and a cutaneous or mucosal surface or wound can be used. Nonlimiting examples of topical formulations for use in the present invention include ointments, creams, lotions, solutions, pastes, gels, emulsions, sprays, aerosols, oils and patches.

In one nonlimiting embodiment, the ISCs and stem cells are coencapsulated. In one nonlimiting embodiment, the ISCs and the stem cells are in a dressing which can be delivered directly to the wound site. In one nonlimiting embodiment, the ISCs and the stem cells are coencapsulated in a dressing which can be delivered directly to the wound site. In another nonlimiting embodiment, the cells are microencapsulated.

A nonlimiting example of a dressing useful in the present invention is a hydrogel dressing.

By "hydrogel" as used herein, it is meant to encompass any three-dimensional, cell-compatible, hydrophilic, polymeric network capable of absorbing large amounts of water or biological fluids. Various types of hydrogel dressings can be used including, but not limited to, amorphous gels, sheets, filler or fiber types of material and gauze types of dressings as well as microsphere/microcapsule suspensions. Hydrogel dressings are designed to hold moisture in the surface of the wound, thus providing an ideal environment for both cleaning the wound and allowing the body to rid itself of necrotic tissue. The moisture in the wound is also essential in pain management for the patient, and these dressings are very soothing and cooling. Their high moisture content also helps to prevent bacteria and oxygen from reaching the wound, thus serving as a barrier against infections. Various hydrogel dressings which can be used in accordance with the present invention to encapsulate cells and heal wounds have been described by, for example, Hunt and Grover (Biotechnology Letter 2010 32(6):733-742) and Seliktar (Science 2012 336(6085):1124-1128). However, as will be understood by the skilled artisan upon reading this disclosure, alternative hydrogel dressings to those disclosed in these references and exemplified herein can be used.

Hydrogel dressings may be of natural or synthetic origin. Nonlimiting examples of natural hydrogels include agarose, alginate, chitosan, collagen, fibrin, gelatin, hyaluronic acid, and laminin. Nonlimiting examples of synthetic hydrogels include polyethylene glycol derivatives including, but not limited to, polyethylene glycol diacrylate (PEGDA), polypropylene oxide, poly(2-acrylamido-2-methylpropanesulfonic acid, polyacrylamide. The hydrogel dressings may include a combination of hydrogels.

In one nonlimiting embodiment, the hydrogel dressing is a sheet with a thickness which maximizes cell viability for at least 10, at least 14 or at least 21 days. Nonlimiting examples include hydrogel sheets ranging in thickness from 300 µm to 500 µm. In one nonlimiting embodiment the hydrogel dressing is a sheet 400 µm in thickness.

In one nonlimiting embodiment, the dressing comprises a bioinert PEGDA hydrogel sheet. Bioinert dressings such as PEGDA hydrogel sheets inhibit migration of the stem cells and/or ISCs.

In another nonlimiting embodiment, the hydrogel may be biodegradable such as, but not limited to, polyethylene glycol (PEG) modified to be biodegradable by inclusion of a peptide cleavable peptide or a hydrolytic portion into the PEG.

In one nonlimiting embodiment, the hydrogel sheet is transparent to allow objective evaluation of the wound without the need for unnecessary dressing changes.

Nonlimiting examples of alternative dressing with can be used include hybrid forms of hydrogel dressings with a hydrocolloid or calcium alginate dressing, hydrocolloid dressings, alginate dressing and collagen dressings.

In one nonlimiting embodiment, the dressing comprises hydrogel microspheres. Nonlimiting examples include PEGDA microspheres.

As shown herein, encapsulation of the ISCs within PEGDA sheets preserves the insulin secretion profile of the ISCs and does not affect free diffusion of glucose and insulin across the porous hydrogel mesh. Further, the insulin and MSC factors released were bioactive and no significant decrease in bioactivity was observed for at least 21 days. The released insulin and MSC factors stimulated both AKT phosphorylation and in vitro keratinocyte migration, each of which is indicative of in vitro wound closure. While hydrogels containing only ISCs at a density of $0.5 \times 10^6$ cells proved to be sufficient to promote AKT phosphorylation and keratinocyte migration, coencapsulation of ISCs and MSCs at a 1:1 ratio and similar cell density promoted AKT phosphorylation and keratinocyte migration at higher levels than either cell used alone.

More specifically keratinocyte scratch assays were conducted to evaluate the biofactors' ability to promote keratinocyte migration. The fastest scratch closure rates were observed with ISC:MSC hydrogels, which were significantly faster than either MSC or ISC hydrogels; the latter two were not statistically distinct from each other. All scratches in keratinocyte monolayers closed significantly faster than controls. ISC:MSC, MSC, and ISC hydrogels closed scratches at rates of 128.6±10.53, 79.02±8.9, and 75.1±6.61 $\mu m/hr/10^6$ cells, respectively, compared to the control rate of $-1.2 \pm 1.7$ $\mu m/hr/10^6$ cells. The scratch closure rates of monolayers treated with ISC hydrogels slowed over time while ISC:MSC and MSC-treated scratches' closure rates did not.

Figure 8:
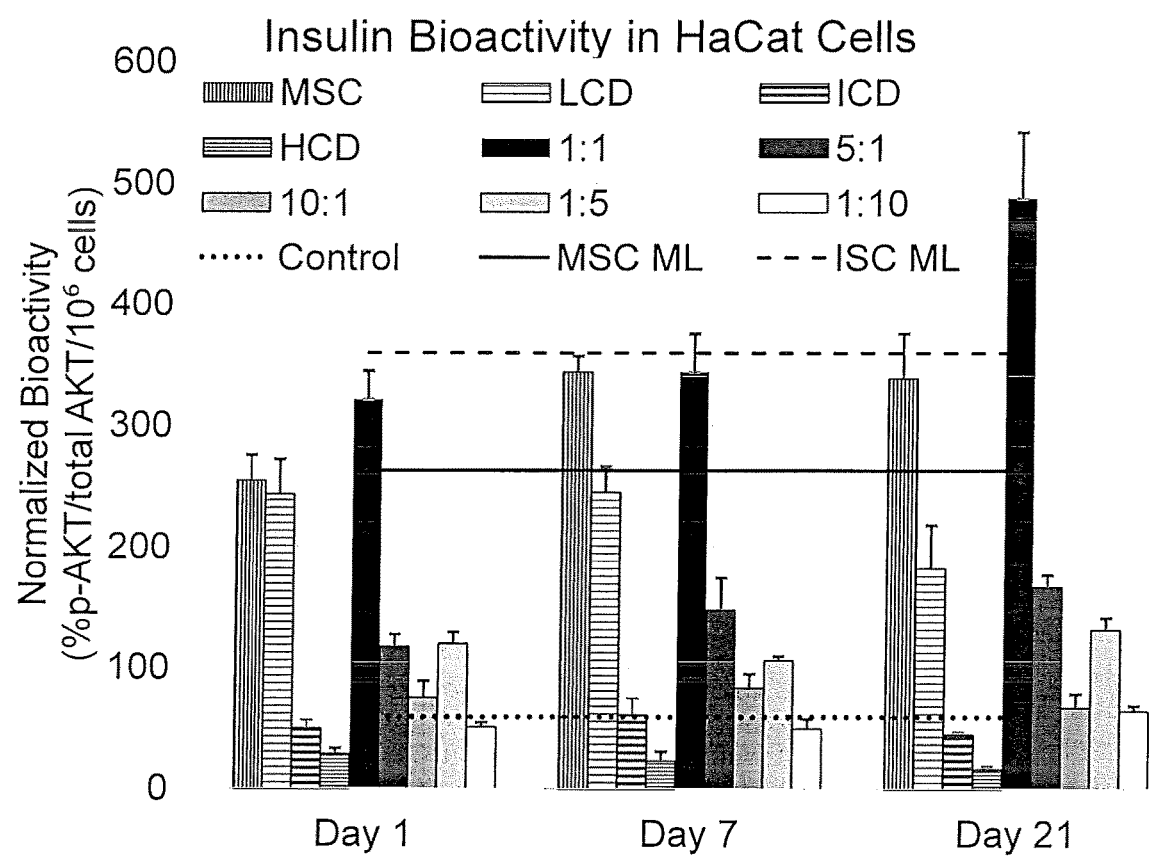
FIG. 8 is a bargraph showing the combination of ISCs and MSCs at a coencapsulation ratio of 1:1 to demonstrate the highest Akt phosphorylation, higher than that achieved when each cell type was encapsulated alone. Dotted line shows control AKT phosphorylation in L6 myoblast cells (no treatment). Dashed line shows Day 1 AKT phosphorylation in cells treated with ISC monolayers. Solid line shows Day 1 AKT phosphorylation in cells treated with MSC monolayers. Vertical striped bar shows Day 1 AKT phosphorylation in cells with encapsulated MSCs; horizontal striped bars show Day 1 AKT phosphorylation in cells with encapsulated ISCs at low, intermediate, and high cell densities (LCD, ICD, and HCD, respectively). Greyscale bars show Day 1 AKT phosphorylation in cells with encapsulated ISC:MSCs at ratios given.

In addition to scratch assays, factor bioactivity was assessed by measuring the levels of phosphorylated antiserine-threonine kinase (p-Akt) produced when L6 myoblasts were exposed to the hydrogels. L6 myoblasts are known to produce p-AKT when stimulated by insulin or MSCs. Akt phosphorylation provides a measure of the bioactivity of insulin and MSC growth factors since both are known to activate the Akt pathway. All cell-laden hydrogels stimulated significant Akt phosphorylation compared to controls; no significant decrease in the levels was observed for the 3-week duration. Phosphorylated Akt induced by ISC:MSC was significantly higher for 21 days compared to all other hydrogel constructs. As shown in FIG. 8, the combination of ISCs and MSCs at a coencapsulation ratio of 1:1 demonstrated the highest Akt phosphorylation, higher than achieved when each cell type was encapsulated alone, thus providing a measure of the unexpected synergy for the combined bioactivity of the two cell types.

Compositions of the present invention were demonstrated to significantly accelerate wound healing as compared to normal wound healing in a diabetic mouse model. Further, the compositions of the present invention accelerated wound healing as compared to wound healing with compositions comprising equivalent amounts of only insulin-secreting cells or only mesenchymal stem cells in these mice. While single-cell therapy with ISCs encapsulated alone in PEDGA hydrogels improved wound healing 1.6 times faster than controls in a diabetic mouse model, the dual-cell therapy of ISC and MSC coencapsulation of the present invention further accelerated wound closure 2.5 times faster. More specifically, healing time of a chronic wound was reduced ~40 to 14 days. In contrast, wounds that were treated with single cells, ISCs or MSCs, did not close until day 28. Thus, the combination of encapsulated ISCs and stems cells such as MSCs of the present invention has been demonstrated to synergistically accelerate wound repair at greater rates than either cell used alone.

Figure 14A:
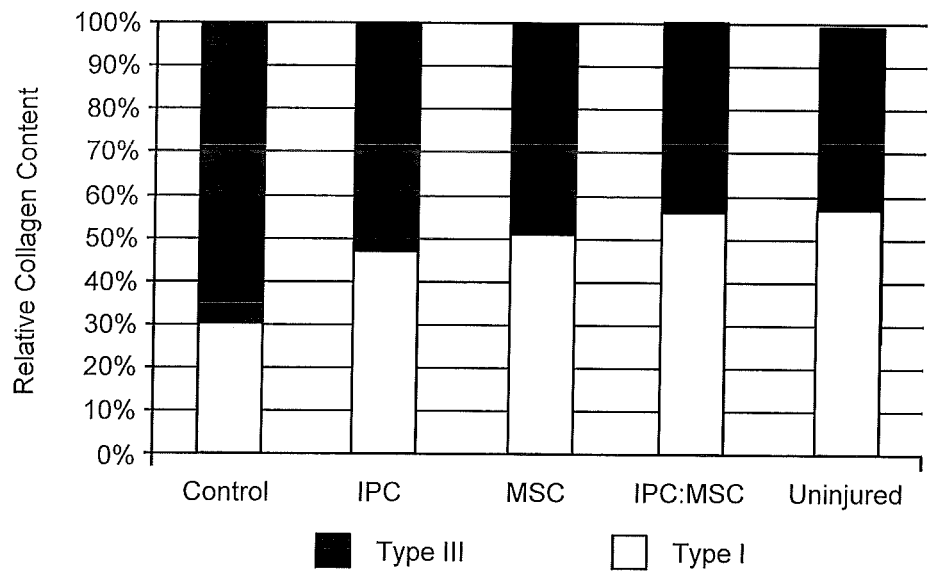
FIGS. 14A and 14B are bargraphs showing quantification of relative content of collagen type I and III in PASR-stained histological sections of wound tissue (FIG. 14A) and collagen type I to III ratio (FIG. 14B). Histological sections were imaged under cross-polars. Dashed line: type I/III ratio in uninjured skin, dotted line: type I/III ratio in control wounds, asterisks: significance vs. control.
Figure 14B:
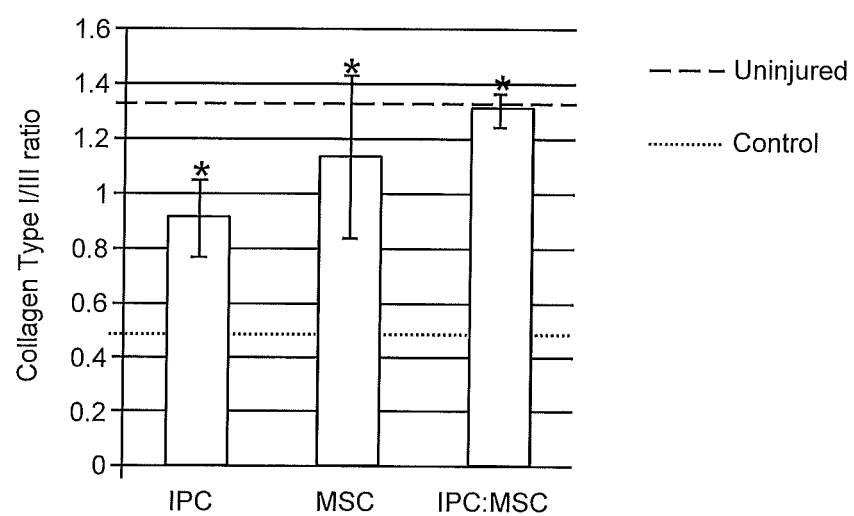

Further, none of the wounds treated with ISC:MSC hydrogels developed visible scabs or scars. Type I and III collagens play a critical role in scar formation; though necessary for wound healing, an excess deposition of collagen can result in scarring (Verhaegen et al. Journal of Microscopy 2012 245(1): 82-89; and Verhaegen et al. Wound Repair and Regeneration 2012 20(5): 658-666. Therefore, a critical balance of type I and III collagen is required for scar-free healing (Oliveira et al. International Wound Journal 2009 6(6):445-452). The collagen in ISC:MSC-treated wounds was less densely packed than other wounds, and the collagen I/III ratio as shown in FIGS. 14A and 14B was identical to that of uninjured skin. Conversely, scars have highly densely packed collagen with a lower collagen I/III ratio than normal skin (Zhang et al. British Journal of Dermatology 1994 130(4):453-459) strongly supporting the visible observation that ISC:MSC wounds healed without scar. Although uninjured skin had a thinner epidermis and dermis than ISC:MSC healed skin, the 28-day harvest date was still within the remodeling phase of the wound. A basket-weave like collagen alignment was observed in uninjured skin and ISC:MSC (1:1) treated wound sections demonstrated a trend towards this basket-weave like alignment. A similar basket-weave trend was observed in MSC treated wound sections; however, the fibers were thinner and immature, while ISC:MSC collagen fibers were thicker and closer in size to uninjured collagen fibers. The basket-weave was absent in other groups. Thin immature collagen fibers in ISC treated wounds were aligned parallel to the epidermis and control wounds were composed of nascent and immature collagen identified as blue to green fibers under cross-polarized light. Histology at day 14 vs day 28 harvests showed continued remodeling suggesting it would continue towards normal skin rather than scar. The scar-free healing observed could revolutionize reconstructive surgery by reducing or eliminating scar formation, thus improving functional and cosmetic outcomes in plastic surgery or for those who suffer from hypertrophic scar.

In addition, these compositions are shown herein to continue to produce insulin and MSC products including, but not limited to TGF-β1 and VEGF, for prolonged periods. Further, coencapsulation improved biofactor release as determined by ELISA assays. The ISC:MSC dual-cell hydrogels that healed wounds faster were shown to release more insulin, VEGF, and TGF-β1 than hydrogels containing singly encapsulated ISCs or MSCs. Over the course of a 3 week in vivo study, insulin secretion levels from ISC-only hydrogels ranged between 7.8-16.3 ng/mL/$10^6$ cells. When ISCs were combined with MSCs, these values increased to 12.9-27.5 ng/mL/$10^6$ cells. Similarly, coencapsulation with ISCs improved growth factor release from MSCs. In MSC-only hydrogels, TGF-β1 levels ranged between secreted 347.1-824.6 pg/mL/$10^6$ cells and when combined with ISCs, these levels increased to 610.4-1,038.4 pg/mL/$10^6$ cells. TGF-β1 levels from monolayer MSCs reached only 161.6±102.3 pg/mL/$10^6$ cells, suggesting that encapsulation in and of itself stimulated TGF-β1 release. Likewise, VEGF release was not detected in MSC monolayers, but was detected in MSC and ISC:MSC hydrogels. VEGF release was also increased when MSCs were coencapsulated with MSCs, from 23.6-341.8. Thus, the compositions of the present invention can be used for the sustained and steady delivery of both insulin and stem cell factors without the need for multiple applications.

Accordingly the compositions of the present invention are useful in methods for healing a wound in a subject. Such methods comprise applying a composition of the present invention directly to the wound site. Wound sites to which the composition may be applied include, but are not limited to, chronic wounds such as diabetic ulcers, pressure ulcers and venous ulcers as well as acute wounds such as thermal and radiation burns and surgical wounds. In addition, the re-epithelialization which occurs during the accelerated wound healing with the compositions of the present invention reduces scar formation and/or scab formation at the wound site.

The following nonlimiting examples are provided to further illustrate the present invention.

EXAMPLES

Example 1: ISC Encapsulation Procedure

Hydrogel precursor solution is prepared by combining 0.2 g/mL 10 kDa PEGDA (10% w/v), 37 mM 1-vinyl-2-pyrrolidinone with hydrophilic photoinitiators (1.5% (v/v) thriethanolamine and 0.1 mM eosin Y) in HEPES-buffered saline (pH 7.4). Cells are harvested, washed, and suspended in PBS following standard techniques to achieve a final concentration of 2,500 cells/μl are then mixed in a 1:1 ratio with the hydrogel precursor. Hydrogel sheets (1 cm×1 cm×300-500 μm) are formed by aliquotting the prepolymer/cell solution into glass/Teflon molds and then photopolymerizing the solution. The hydrogels are polymerized by exposing the molds to white light for 30 seconds. The hydrogel sheets are removed from the molds and placed in a flask of culture medium to swell for 24 hours.

Example 2: Optimization of Hydrogel Sheet Thickness to Maximize Encapsulated ISC Cell Viability Hydrogels sheets with thicknesses of 300, 400 or 500 μm and encapsulated ISC cells at low cell density (LCD: 0.5× $10^6$ cells), intermediate cell density (ICD; 2×$10^6$ cells) and high cell density (HCD; 5×$10^6$ cells) were stained for viability using Invitrogen's LIVE/DEAD® Viability/Cytotoxicity Kit, for mammalian cells and incubated in calcein AM and ethidium homodimer 1 according to manufacturer's instructions. Z-stack images were then acquired via Apotome under an epifluorescent microscope and live and dead cells were assessed. Results from these experiments are depicted in FIG. 1. Cells maintained the highest viability in 400 μm sheets. ISC viability on day 1 was 82.6±2.2%, 85.3±9% and 75.1±11.1% for LCD, ICD and HCD, respectively.

Example 3: Glucose-Stimulated Insulin Release in Encapsulated ISCs

Figure 2:
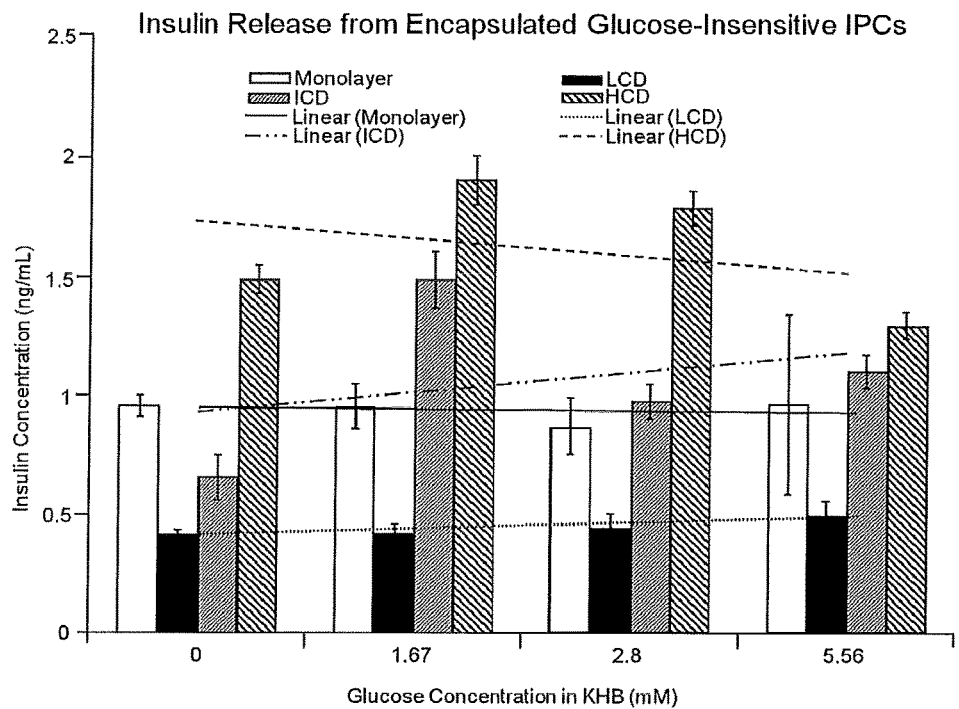
FIG. 2 is a bargraph depicting results of glucose stimulated insulin secretion of ISCs at low, intermediate and high cell density encapsulated on 400 μm thick hydrogel sheets. The bar graphs show the data, the trendlines show that the encapsulated ISCs are not increasing their insulin release with increased glucose.

LCD, ICD and HCD ISC hydrogel constructs were maintained in Krebs-Henseleit buffer (KHB) without glucose for 60 minutes, then stimulated with incremental glucose concentrations of 1.67, 2.8 and 5.56 mM in KHB. Each concentration was used to perform static glucose incubations with each hydrogel constructs for 2 hours. Secreted insulin was assessed using a commercial ELISA kit (EMD Millipore). Results are depicted in FIG. 2. As shown therein insulin secretory characteristics of ISCs were preserved in the 400 μm sheets. Average insulin secretion levels were 0.45 ng/ml, 1.06 ng/ml and 1.62 ng/ml in LCD, ICD and HCD sheets, respectively.

Example 4: ISC/MSC Coencapsulation Procedure

Hydrogel precursor solution is prepared by combining 0.2 g/mL 10 kDa PEGDA (10% w/v), 37 mM 1-vinyl-2-pyrrolidinone with hydrophilic photoinitators (1.5% (v/v) thriethanolamine and 0.1 mM eosin Y) in HEPES-buffered saline (pH 7.4). Cells are harvested, washed, and suspended in PBS following standard techniques to achieve a final concentration of 1,250 cells/μl for each cell type. Cells are combined, then mixed in a 1:1 ratio with the hydrogel precursor. Hydrogel sheets (1 cm×1 cm×400 μm) are formed by aliquotting the prepolymer/cell solution into glass/Teflon molds and then photopolymerizing the solution. The hydrogels are polymerized by exposing the molds to white light for 30 seconds. The hydrogel sheets are removed from the molds and placed in a flask of culture medium to swell for 24 hours.

Example 5: Insulin Release in Coencapsulated ISCs/MSCs

Figure 3:
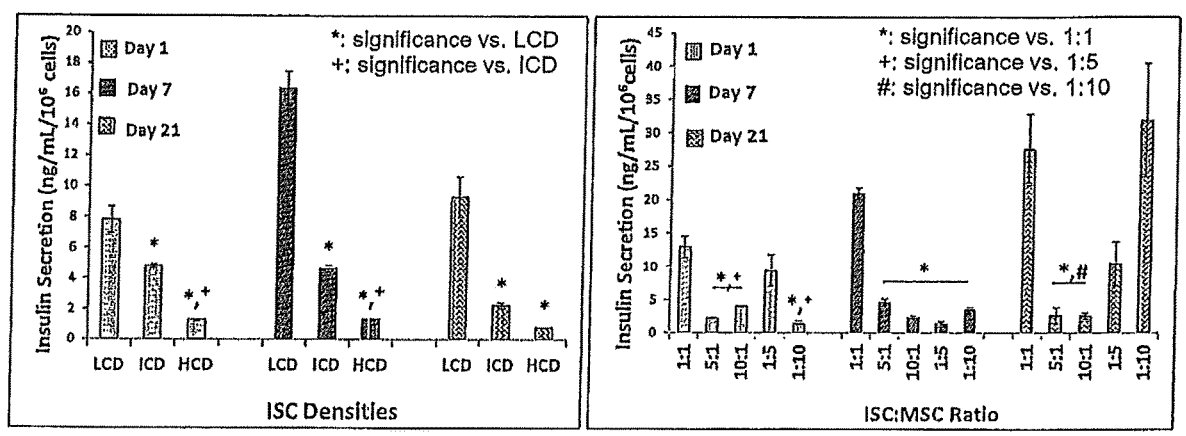
FIG. 3 provides two bargraphs comparing insulin secretion in ISC-MSC coencapsulated constructs based upon ISC cell density and ISC:MSC ratios.
Figure 4:
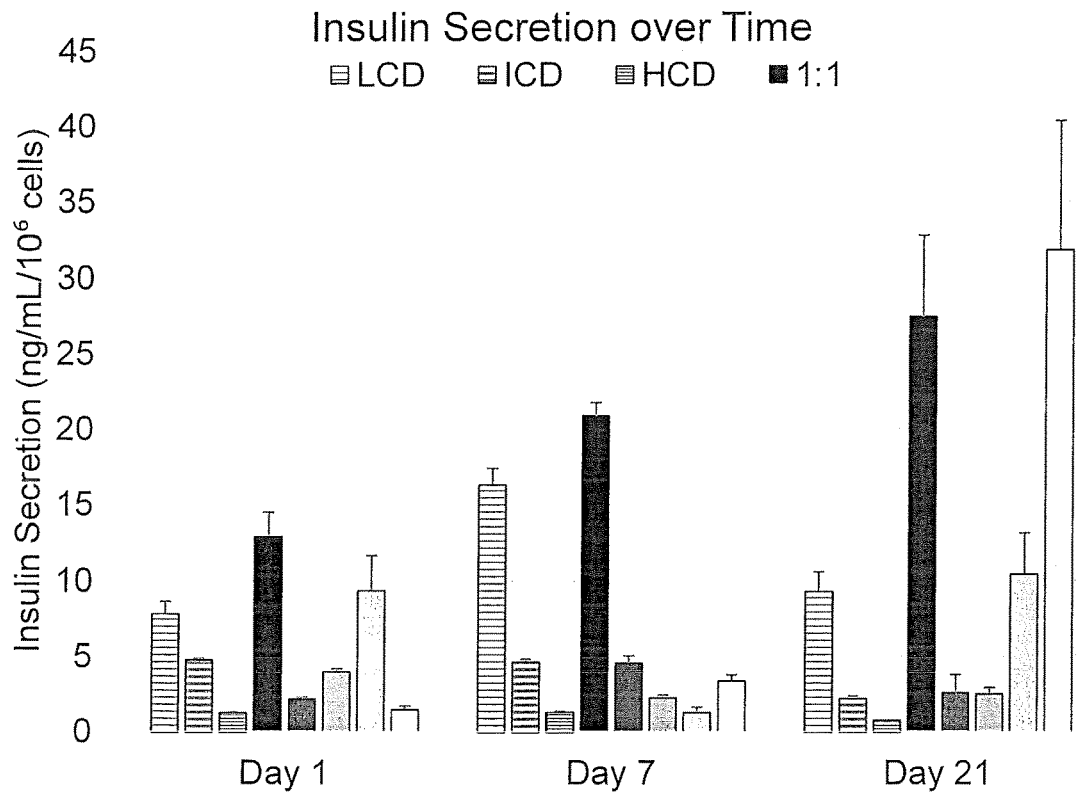
FIG. 4 is a bargraph showing improved insulin secretory function of ISCs upon coencapsulation with MSCs.

Encapsulated cells were maintained in culture in humidified incubators with 5% $CO_2$. Insulin released into media was measured by ELISA kit according to manufacturer's instructions. Media was changed every other day, such that odd days had 24 hours insulin accumulation in the media. Media were collected on days 1, 7, and 21. Results are depicted in FIGS. 3 and 4. As shown in FIG. 3, highest insulin secretion was achieved at low cell densities and at low coencapsulation ratios. This is in agreement with the observation that islets are known to undergo hypoxia-induced cell death when cultured at high cell densities (see Pedraza et al. PNAS 2012 109(11)4245-4250). Further, as shown in FIG. 4, insulin secretory performance of ISC:MSC coencapsulation constructs was significantly higher than their ISC alone cell-density equivalents (1:1 vs LCD and 5:1 vs HCD). The 1:1 construct outperformed in insulin secretion function compared to all other constructs, followed by the LCD construct.

Example 6: Determination of MSC Factor Release

Figure 5:
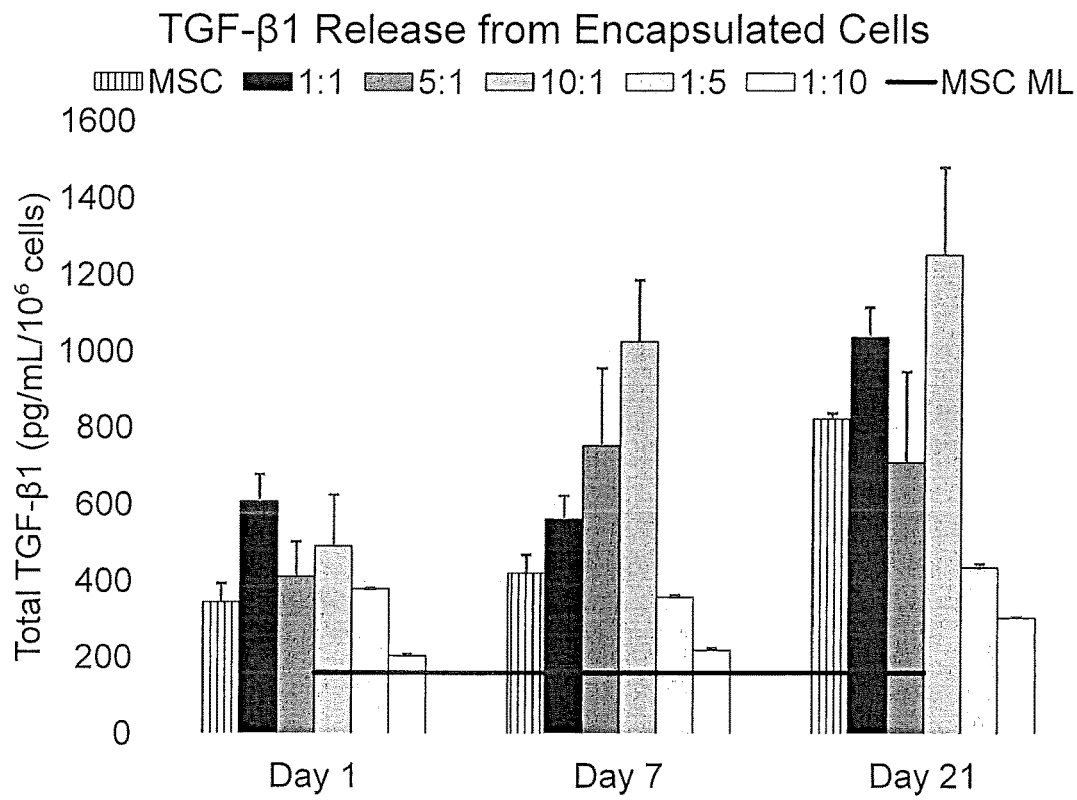
FIG. 5 is a bargraph showing TGF-β1 concentrations secreted from MSCs in coencapsulates at densities of 1:1, 5:1 and 10:1 ISCs:MSCs at day 1, day 7 and day 21. Solid line shows TGF-β1 release from MSC monolayers. Vertical striped bar shows TGF-β1 release from encapsulated MSCs. Greyscale bars show TGF-β1 release from encapsulated ISC:MSCs at ratios given.
Figure 6:
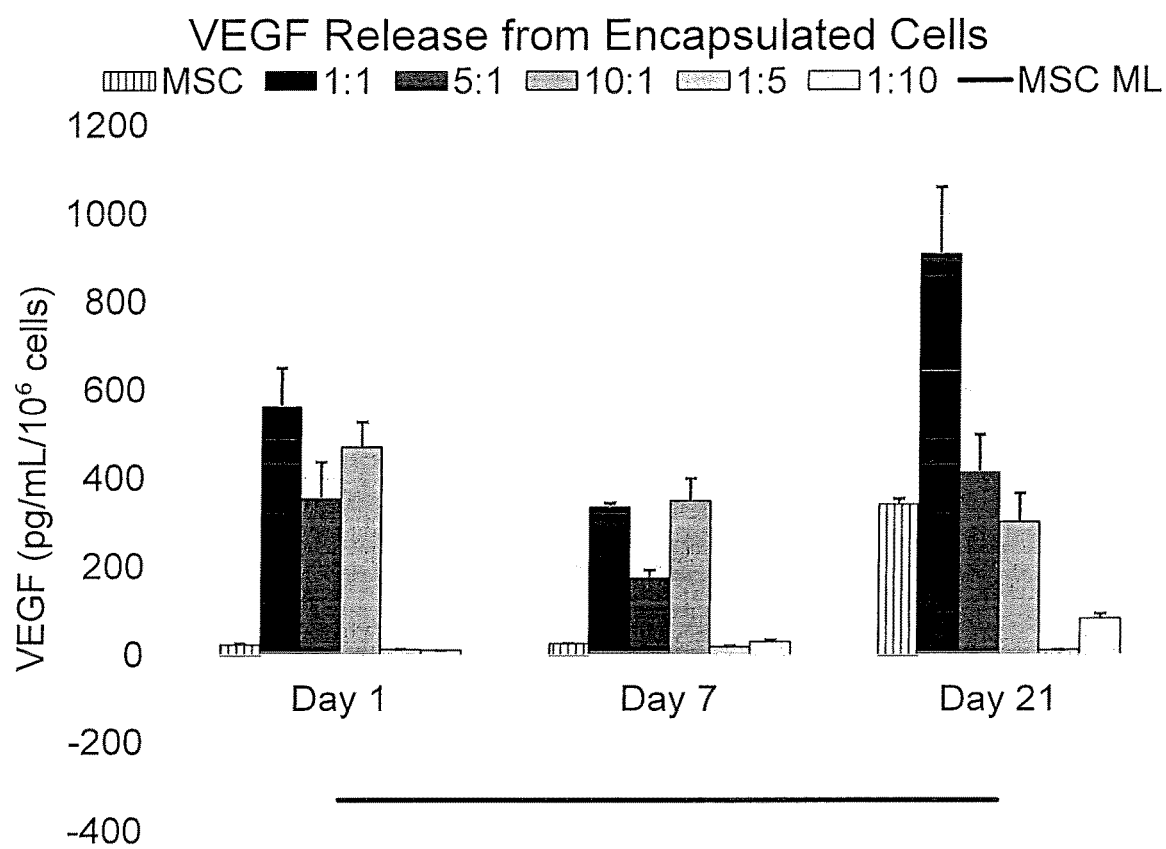
FIG. 6 is a bargraph showing VEGF concentrations secreted from MSCs in coencapsulates at densities of 1:1, 5:1 and 10:1 ISCs:MSCs at day 1, day 7 and day 21. Solid line shows VEGF release from MSC monolayers. Vertical striped bar shows VEGF release from encapsulated MSCs. Greyscale bars show VEGF release from encapsulated ISC:MSCs at ratios given.

Encapsulated cells were maintained in culture in humidified incubators with 5% $CO_2$. VEGF and TGF-β1 released into media was measured by ELISA kit according to manufacturer's instructions. Media was changed every other day, such that odd days had 24 hours insulin accumulation in the media. Media were collected on days 1, 7, and 21. Results are depicted in FIGS. 5 and 6. As shown therein, ISC:MSC constructs demonstrated high MSC factor release of both TGF-β1 and VEGF until day 21. More specifically, as shown in FIG. 5, TGF-β1 secretion increased with increasing ISC density. TGF-β1 levels are known to preserve and prolong survival of islets. As shown in FIG. 6, VEGF release was not detected in MSC monolayers, but was in ISC:MSC hydrogels; MSC are known to secrete VEGF to promote islet vascularization.

Example 7: Assessment of Insulin and MSC Factor Bioactivity Via FACE AKT ELISA

Figure 7:
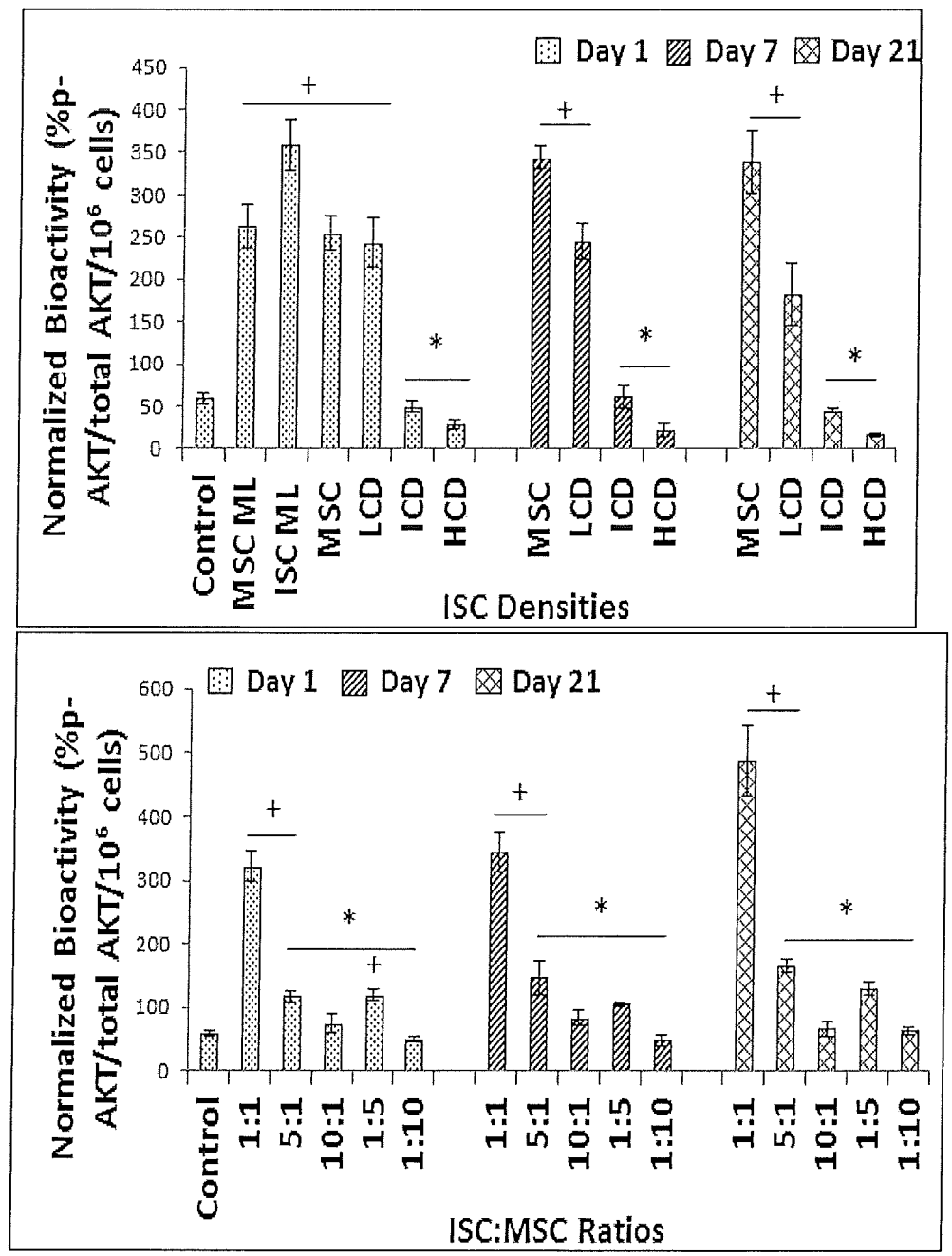
FIG. 7 provides two bargraphs comparing insulin-stimulated Akt phosphorylation in ISC-MSC coencapsulated constructs based upon ISC cell density and ISC:MSC ratios.

L6 Myoblasts were maintained in culture and stimulated with media collected from hydrogels with encapsulated cells. Media used was collected on days 1, 7, and 21. Because insulin stimulates keratinocyte differentiation and migration, which is dependent on activation of the PI3K-Akt pathway, Akt phosphorylation was assessed with FACE AKT ELISA kits.
Results are depicted in FIGS. 7 and 8. In FIG. 7, % Akt phosphorylation was normalized to the encapsulated cell number. As shown therein, LCD, 1:1 and 5:1 hydrogel constructs were significant to control hydrogels. Further, among the ISC alone constructs, LCD hydrogels outperformed compared to higher encapsulated cell density (ICD, HCD) hydrogels. However, the 1:1 coencapsulation construct outperformed all other constructs. As shown in FIG. 8, the combination of ISCs and MSCs at a coencapsulation ratio of 1:1 demonstrated the highest Akt phosphorylation, higher than that achieved when each cell type was encapsulated alone.

Figure 9:
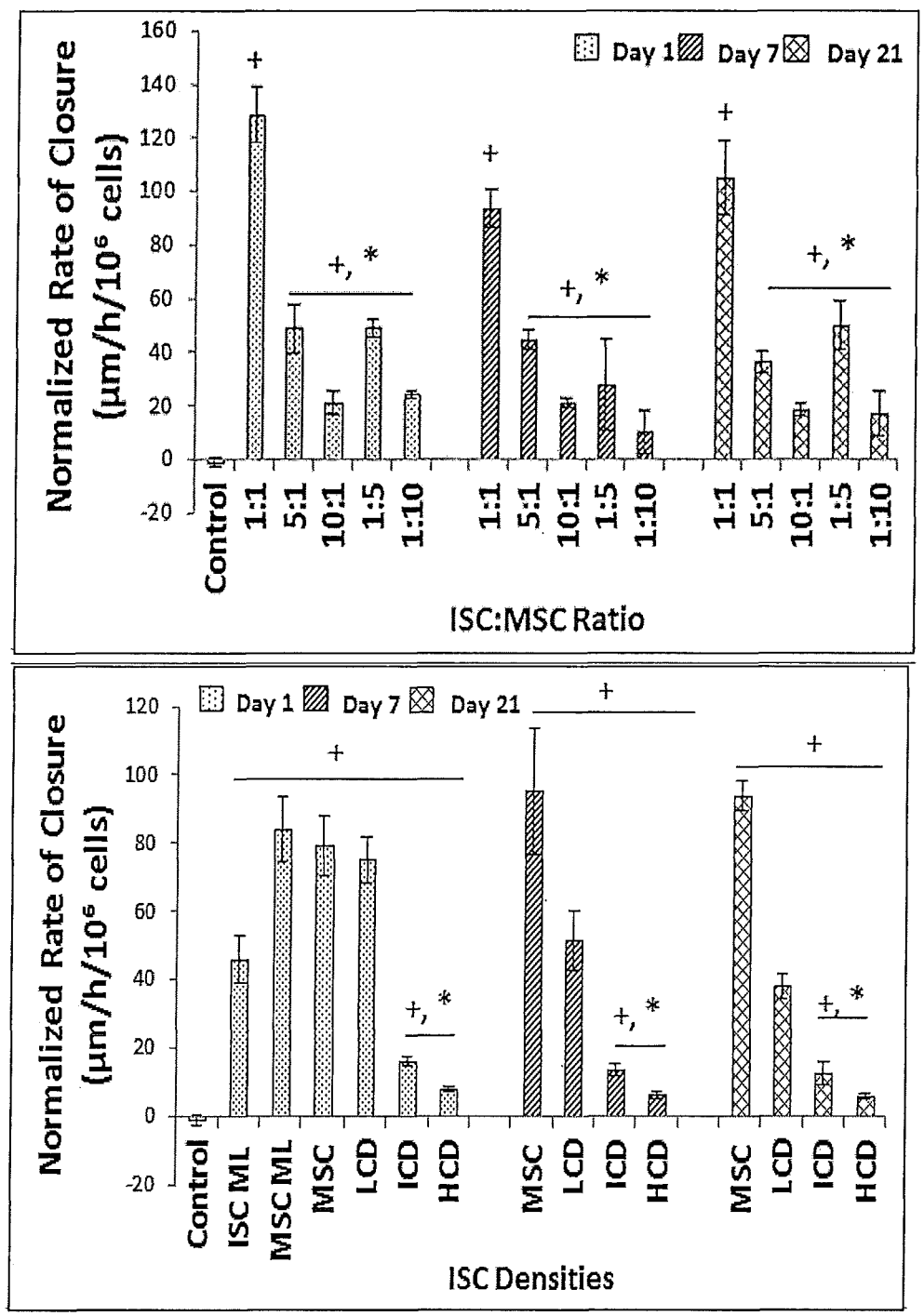
FIG. 9 provides two bargraphs of the assessment of in vitro Scratch wound closures in ISC-MSC coencapsulated constructs based upon ISC cell density and ISC:MSC ratios.
Figure 10:
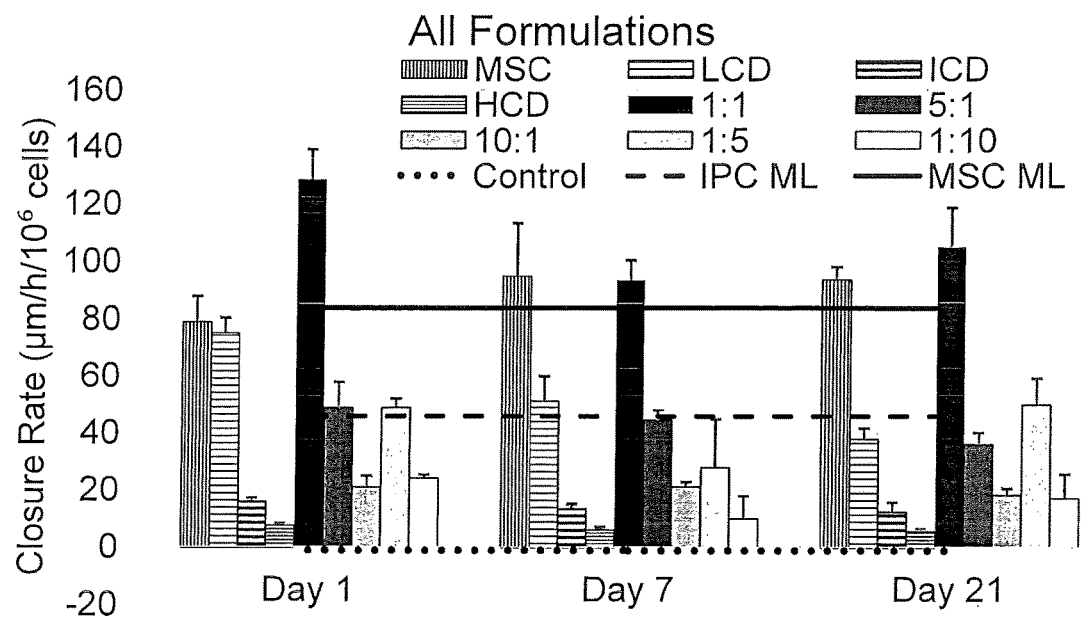
FIG. 10 is a bargraph showing coencapsulation of ISCs with MSCs to improve scratch wound closures. Dotted line shows control rate of closure (no treatment). Dashed line shows Day 1 closure rate for scratches treated with ISC monolayers. Solid line shows Day 1 closure rate for scratches treated with MSC monolayers. Vertical striped bar shows closure rate with encapsulated MSCs; horizontal striped bars show closure rate with encapsulated ISCs at low, intermediate, and high cell densities (LCD, ICD, and HCD, respectively). Greyscale bars show closure rate with encapsulated ISC:MSCs at ratios given.

Example 8: Assessment of Insulin and MSC Factor Bioactivity Via Keratinocyte Scratch Assay HaCaT keratinocyte migration was assessed via image analysis. Confluent HaCaT monolayers were scratched with a pipet tip and allowed to close with no treatment, or in the presence of media collected from hydrogel constructs. Media were collected from these constructs on Days 1, 7, and 21. Results are depicted in FIGS. 9 and 10. For FIG. 9, the rates of in vitro scratch closures were normalized to the encapsulated cell number. As shown therein, among the ISC alone constructs, LCD hydrogels outperformed compared to higher encapsulated cell density hydrogels. However, the 1:1 coencapsulation construct outperformed all other construct. Further, as shown in FIG. 10, the combination of ISCs and MSCs at a coencapsulation ratio of 1:1 demonstrated the fastest closure rate, higher than that achieved when each cell type was encapsulated alone.

Example 9: Determination of Wound Healing Response In Vivo

Figure 11:
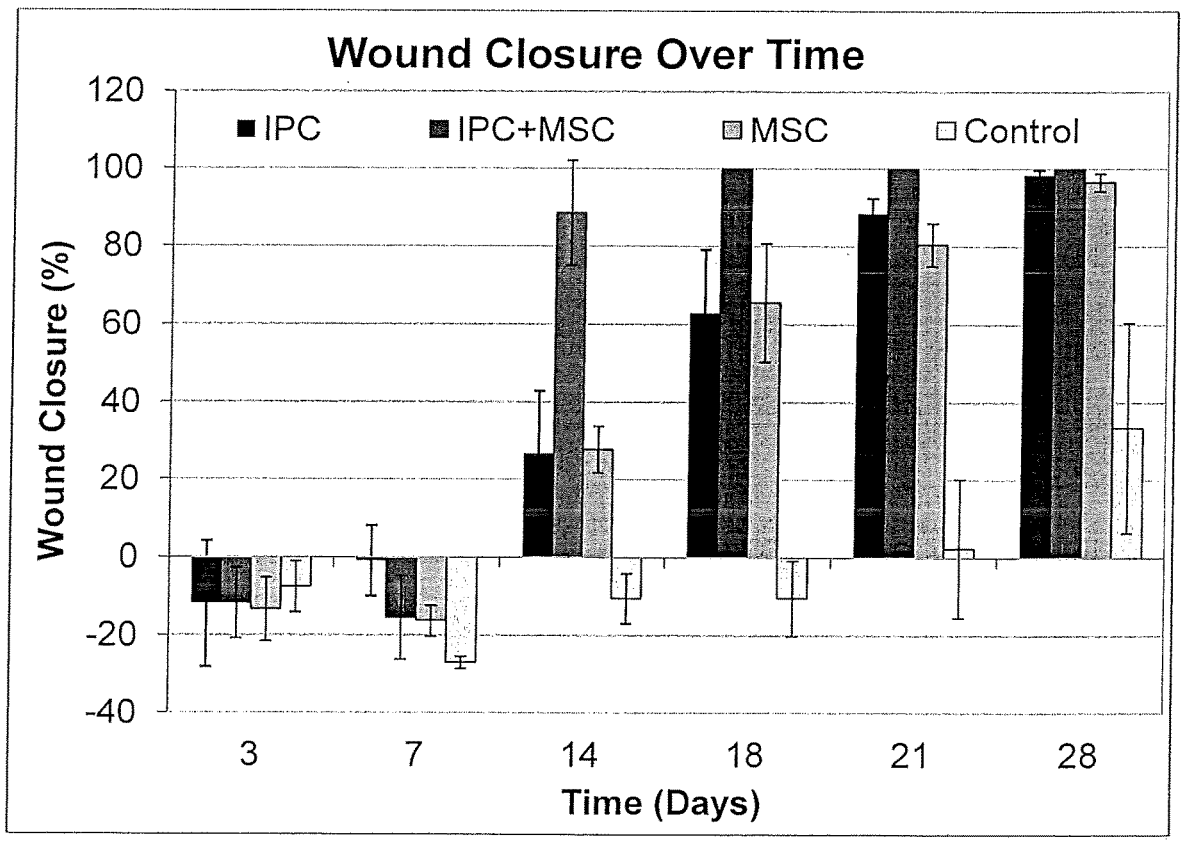
FIG. 11 is a bargraph showing wound healing in a mouse model.
Figure 13:
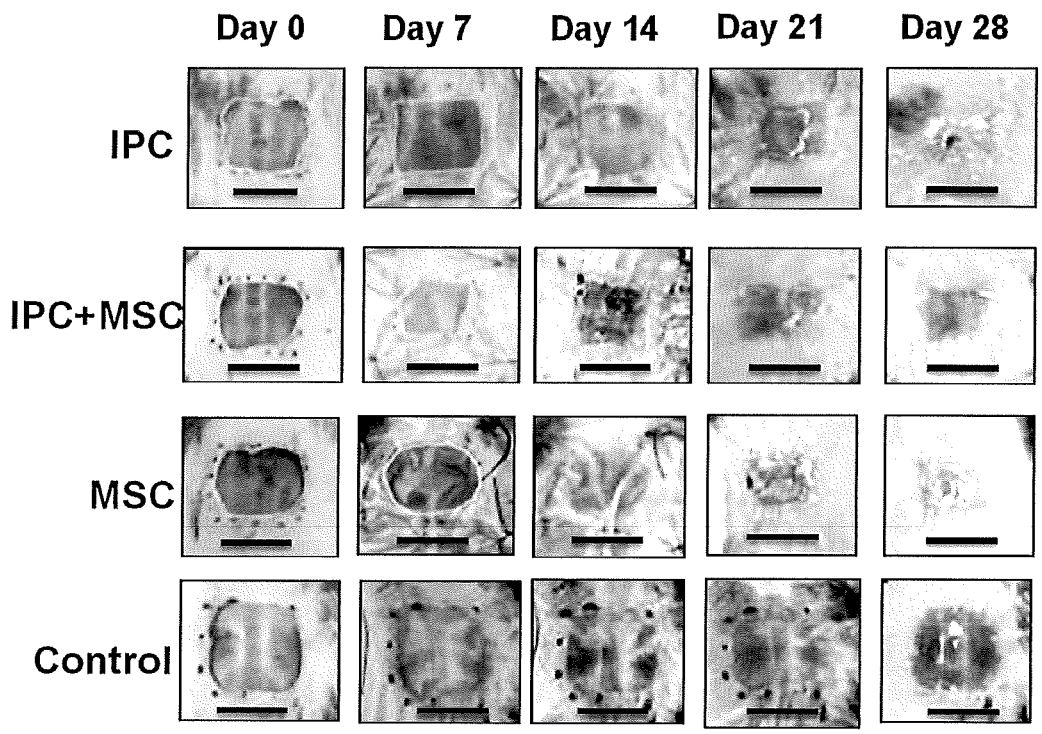
FIG. 13 shows photographs of wound healing in mice treated with ISCs alone, ISCs:MSCs and MSCs alone as well as a control as Day 0, 7, 14, 21 and 28. Arrows show scabs in groups except ISC+MSC, which did not form scabs, and control, which did not heal.

Wound healing was measured in vivo in genetically diabetic mice (see Aijaz et al. Tissue Engineering Part A 2015 21(21-22):2723-2732; Wetzlet et al. Journal of Investigative Dermatology 2000 115(2):245-253; Werner et al. Journal of Investigative Dermatology 1994 103(4):469-473). A full thickness wound was created on the back of the mouse. Treatment hydrogels containing ISCs alone, a coencapsulate of 1:1 ISCs:MSCs or MSCs alone, or a control, unladen, hydrogel was then applied to the wound. 6 animals are in each treatment group with 2 sacrifice time points, Day 14 (n=3) and Day 28 (n=3). Gross examination and imaging were performed at days 3, 7, 14, 18, 21 and 28. Wound tissue samples from sacrificed animals were collected for histological and Western Blot Analysis. Results of the wound healing response as determined by gross examination and imaging are depicted in FIG. 11. As shown therein, single-cell therapy with ISCs encapsulated alone in PEDGA hydrogels improved wound healing 1.6 times faster than controls in a diabetic mouse model. The dual-cell therapy of ISC and MSC coencapsulation further accelerated wound closure 2.5 times faster. Complete closure was achieved on POD 18 in all animals treated with ISC:MSC (1:1), a significant difference compared to all other groups, which were still open on POD 28. FIG. 13 shows photographs of wound healing in these mice. Scabs formed in groups treated with hydrogels containing ISCs alone and MSCs alone. Scab formation was inhibited during wound healing in mice treated with ISC+MSC. Control mice showed no healing or scab formation.

Example 10: Blood Glucose Analysis

Figure 12:
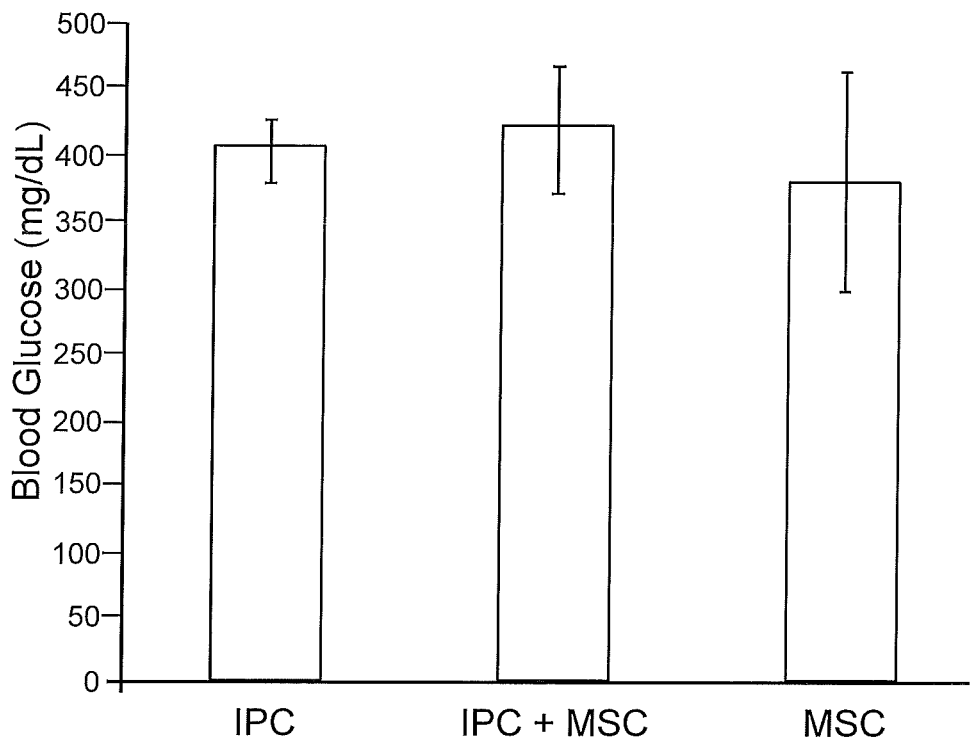
FIG. 12 is a bargraph showing glucose levels in mice treated with ISCs alone, ISCs:MSCs and MSCs alone.

To ensure that improved wound healing was not as a result of lowered blood glucose levels, blood glucose was measured in mice of Example 10. At sacrifice, blood was removed from tail veins and applied to test strips and read by an electronic glucometer. As shown in FIG. 12, blood glucose levels in the mice were unaffected by the treatment.

Example 11: Histological Analysis

After sacrifice, wound tissue was explanted, fixed in 10% formalin for 24 hours at room temperature, then stored in 70% ethanol at 4° C. until serial sectioning (5 μm thick). Then wounds were sectioned and stained with hematoxylin and eosin (H & E) for morphological analysis, picric acid sirius red (PASR) for collagen fiber density, Ki67 for cell proliferation, and alpha smooth muscle actin (α-SMA) for wound contraction at the Digital Imaging and Histology Core, Rutgers-NJMS Cancer Center. Histological images were analyzed on ImageJ software to determine epidermal and dermal thickness and collagen density. RGB images of PASR-stained sections were converted to gray scale by splitting the images into red, green and blue channels. Thresholded images were analyzed to measure percent area of collagen density (Hunter et al. PLOS ONE 2012 7(5): e36893). PASR stained histology slides were also imaged under cross-polars for collagen birefringence.

Example 12: Statistics

All data is measured in triplicate and reported as mean±standard deviation. One-way analysis of variance (ANOVA) is performed using p-values of <0.05 for statistical significance. Pairwise comparisons are made between groups using Fisher's Least Significant Difference (LSD) post-hoc test. For in vivo evaluation of wound healing studies, 6 animals per treatment group are used.

What is claimed is:

1. A composition for healing wounds, said composition comprising coencapsulated or microencapsulated insulin-secreting cells and stem cells in a hydrogel dressing.

2. The composition of claim 1 wherein the hydrogel dressing is a hydrogel sheet.

3. The composition of claim 2 wherein the hydrogel sheet has a thickness which maximizes cell viability for at least 10 days.

4. The composition of claim 2 wherein the hydrogel sheet has a thickness which maximizes cell viability for at least 21 days.

5. The composition of claim 2 wherein the hydrogel sheet ranges in thickness from 300 μm to 500 μm.

6. The composition of claim 1 wherein the insulin-secreting cells and the stem cells are included in the composition in an amount effective to produce re-epithelialization at the wound site.

7. The composition of claim 1 which delivers bioactive insulin-secreting and stem cell products to a wound site for a prolonged period of time.

8. The composition of claim 7 which delivers bioactive insulin-secreting and stem cell products to a wound site for at least 21 days.

9. The composition of claim 1 wherein the cells are included at an insulin-secreting cell to stem cell ratio effective at promoting AKT phosphorylation and/or keratinocyte migration at levels higher than either cell when used alone.

10. The composition of claim 9 wherein the insulin-secreting cell to stem cell ratio ranges from 1:10 to 10:1.

11. A method for healing a wound in a subject, said method comprising applying the composition of claim 1 to a wound site of the subject.

12. The method of claim 11 which accelerates wound healing as compared to normal wound healing and wound healing with compositions comprising only insulin-secreting cells or only mesenchymal stem cells.

13. A method for reducing scar formation and/or scab formation at a wound site in a subject, said method comprising applying the composition of claim 1 to a wound site of the subject.

14. A method for accelerating wound healing in a subject, said method comprising delivering insulin and stem cell products to a wound site in the subject.

15. The method of claim 14 wherein the insulin is delivered via insulin-secreting cells and/or the stem cell products are delivered via mesenchymal stem cells.

16. The method of claim 14 wherein the insulin and stem cell products are delivered to the wound site via a topical composition comprising insulin-secreting cells and mesenchymal stem cells.

17. The composition of claim 1 wherein the stem cells comprise mesenchymal stem cells.

* * * * *